United States Patent
Kudoh et al.

(10) Patent No.: US 11,168,300 B2
(45) Date of Patent: Nov. 9, 2021

(54) MICROORGANISM AND PRODUCTION METHOD FOR UROLITHINS USING SAME

(71) Applicant: DAICEL CORPORATION, Osaka (JP)

(72) Inventors: Masatake Kudoh, Niigata (JP); Takanori Nakajima, Niigata (JP); Hiroaki Yamamoto, Niigata (JP)

(73) Assignee: DAICEL CORPORATION, Osaka (JP)

( * ) Notice: Subject to any disclaimer, the term of this patent is extended or adjusted under 35 U.S.C. 154(b) by 0 days.

(21) Appl. No.: 16/536,056

(22) Filed: Aug. 8, 2019

(65) Prior Publication Data

US 2019/0359932 A1 Nov. 28, 2019

Related U.S. Application Data

(63) Continuation of application No. PCT/JP2018/006192, filed on Feb. 21, 2018.

(30) Foreign Application Priority Data

Feb. 23, 2017 (JP) .............................. JP2017-031674

(51) Int. Cl.
*C12N 1/20* (2006.01)
*C12P 17/06* (2006.01)
*C12R 1/01* (2006.01)

(52) U.S. Cl.
CPC ............... *C12N 1/20* (2013.01); *C12N 1/205* (2021.05); *C12P 17/06* (2013.01); *C12R 2001/01* (2021.05)

(58) Field of Classification Search
CPC ............ C12N 1/20; C12N 1/205; C12P 17/06; C12R 1/01; C12R 2001/01
USPC ......................................................... 435/41
See application file for complete search history.

(56) References Cited

FOREIGN PATENT DOCUMENTS

| EP | 3561067 A1 | 10/2019 |
| WO | WO 2007/114519 A1 | 10/2007 |
| WO | WO 2014/147280 A1 | 9/2014 |

OTHER PUBLICATIONS

Dhand, Which fruits contain the most water?, Jul. 9, 2012, Available online at: suneeldhand.com/2012/07/09/which-fruits-contain-the-most-water/.*
Selma et al., "*Gordonibacter urolithinfaciens* sp. nov., a urolithin-producing bacterium isolated from the human gut", International Journal of Systematic and Evolutionary Microbiology (2014), 64, 2346-2352.
Selma et al., "Isolation of Human Intestinal Bacteria Capable of Producing the Bioactive Metabolite Isourolithin A from Ellagic Acid", Frontiers in Microbiology, vol. 8, Article 1521, 2017.
Extended Search Report issued in corresponding EP patent application No. 18756796.1, dated Oct. 19, 2020.
Hideyuki Ito et al., J. Agric. Food Chem. 2008, 56, 393-400.
Maria A. Nunez-Sanchez et al., Mol. Nutr. Food Res. 2014, 58, 1199-1211.
Hidekazu Ishimoto et al., Biosci. Biotechnol. Biochem, 76 (2) f 395-399, 2012.
Juan A. Gimenez-Bastida et al., J. Agric. Food Chem. 2012, 60, 8866-8876.
Elena Verzelloni et al., Mol. Nutr. Food Res. 2011, 55 S35-S43.
Hideyuki Ito, Planta Med 2011, 77, 1110-1115.
Maria V. Selma et al., Food Funct. 2014, 5, 1779-1784.
International Search Report issued in PCT/JP2018/006192 dated May 29, 2018.
International Preliminary Report on Patentability in PCT/JP2018/006192 dated Sep. 6, 2019.

* cited by examiner

*Primary Examiner* — Jennifer M. H. Tichy
(74) *Attorney, Agent, or Firm* — Knobbe, Martens, Olson & Bear LLP

(57) ABSTRACT

The present invention addresses the issue of providing: a novel microorganism having a high capability to produce urolithins; and a method of producing urolithins using the same, and the issue is solved by a microorganism that belongs to the genus *Eggerthella* and produces urolithins.

13 Claims, No Drawings

Specification includes a Sequence Listing.

SEQUENCE LISTING

```
<160> NUMBER OF SEQ ID NOS: 1

<210> SEQ ID NO 1
<211> LENGTH: 1464
<212> TYPE: DNA
<213> ORGANISM: Eggerthella sp.

<400> SEQUENCE: 1
gatgaacgct ggcggcgtgc ctaacacatg caagtcgaac gatgaaaccg ccctcgggcg      60
gacatgaagt ggcgaacggg tgagtaacac gtgaccaacc tgcccttgc tccgggacaa     120 ccttgggaaa ccgaggctaa taccggatac tcctcgcccc cctcctgggg ggcccgggaa    180
agcccagacg gcaagggatg gggtcgcggc ccattaggta gtaggcgggg taacggccca    240
cctagcccgc gatgggtagc cgggttgaga gaccgaccgg ccacattggg actgagatac    300
ggcccagact cctacgggag gcagcagtgg ggaattttgc gcaatggggg aaaccctgac    360
gcagcaacgc cgcgtgcggg acgacggcct tcgggttgta aaccgctttc agcagggaag    420
aaattcgacg gtacctgcag aagaagctcc ggctaactac gtgccagcag ccgcggtaat    480
acgtagggag cgagcgttat ccggattcat tgggcgtaaa gagcgcgtag gcggcctctc    540
aagcgggatc tctaatccga gggctcaacc cccggccgga tcccgaactg ggaggctcga    600
gttcggtaga ggcaggcgga attcccggtg tagcggtgga atgcgcagat atcgggaaga    660
acaccgatgg cgaaggcagc ctgctgggcc gcaactgacg ctgaggcgcg aaagctaggg    720
gagcgaacag gattagatac cctggtagtc ctagccgtaa acgatggata ctaggtgtgg    780
ggggctccgc cctccgtgcc gcagccaacg cattaagtat cccgcctggg gagtacggcc    840
gcaaggctaa aactcaaagg aattgacggg ggcccgcaca agcagcggag catgtggctt    900
aattcgaagc aacgcgaaga accttaccag ggcttgacat ggacgtgaag ccggggaaac    960
```

```
ccggtggccg agaggagcgt ccgcaggtgg tgcatggctg tcgtcagctc gtgtcgtgag    1020
atgttgggtt aagtcccgca acgagcgcaa cccctgcccc atgttgccag cattaggttg    1080
gggactcatg ggggactgcc ggcgtcaagc cggaggaagg tggggacgac gtcaagtcat    1140
catgcccttt atgccctggg ctgcacacgt gctacaatgg ccggtacaac gggctgcgag    1200
accgcgaggt cgagcgaatc cctcaaagcc ggccccagtt cggatcggag gctgcaaccc    1260
gcctccgtga agtcggagtt gctagtaatc gcggatcagc atgccgcggt gaatacgttc    1320
ccgggccttg tacacaccgc ccgtcacacc acccgagtcg tctgcacccg aagccgccgg    1380
ccgaacccgc aagggcgga ggcgtcgaag gtgtggaggg taaggggggt gaagtcgtaa    1440
caaggtagcc gtaccggaag gtgc                                          1464
```

MICROORGANISM AND PRODUCTION METHOD FOR UROLITHINS USING SAME

CROSS-REFERENCE TO RELATED APPLICATIONS

This application is a continuation application, and claims benefit under 35 U.S.C. §§ 120 and 265 of PCT Application No. PCT/JP2018/006192, filed Feb. 21, 2018, which claims priority to Japanese Patent Application No. 2017-031674, filed Feb. 23, 2017, the contents of which are incorporated by reference herein in their entireties.

FIELD

The present invention relates to a novel microorganism and a method of producing urolithins using the same.

RELATED ART

Urolithins such as urolithin A and urolithin C are known as metabolites of ellagic acid derived from, inter alia, ellagitannins included in pomegranates, raspberries, blackberries, cloudberries, strawberries, walnuts, and the like.

Ellagitannins belong to the class of hydrolyzable tannins, and it is known that when ingested, ellagitannins are hydrolyzed in the body and converted to ellagic acid. Ellagitannins are also present as ellagic acid in fruit and the like. Such ellagitannins and ellagic acids are very poorly absorbed at an intestinal tract of a body, but they are known to be further metabolized by human colon microflora and converted to urolithins when ingested.

For example, regarding the production of urolithins in vivo, it has been reported that the production of urolithins was confirmed by analysis of the urolithins in urine after feeding ellagitannins such as geraniin to rats (Non-Patent Document 1).

It has also been reported that after a human subject consumed a pomegranate extract containing ellagitannins including mainly punicalagin, urolithins were detected in urine, and in particular urolithin A and urolithin C were the major metabolites of ellagic acid (Non-Patent Document 2).

Furthermore, urolithin A has been reported to have functions such as an antioxidant effect (Non-Patent Document 3), an anti-inflammatory effect (Non-Patent Document 4), an anti-glycation effect (Non-Patent Document 5), and a mitophagy-promoting effect (Non-Patent Document 6), and urolithin A is expected to be developed as a material having an anti-aging function.

As a synthesis method for these urolithins, a method has been reported in which 2-bromo-5-methoxybenzoic acid as a starting material is converted to 2-bromo-5-hydroxybenzoic acid via demethylation, and reacted with resorcinol to form urolithin A (Non-Patent Document 1). However, chemical synthesis is not suitable for the purpose of using urolithins as materials for functional food products (including beverages and supplements).

In recent years, a method has been reported in which Gordonibacter urolithinfaciens is isolated and identified as an enteric bacterium that produces urolithin C, which is a type of urolithin, from ellagic acid, and ellagic acid is fermented with the enteric bacterium to thereby produce urolithin C (Patent Document 1 and Non-Patent Document 7). However, the concentration of urolithin C accumulated in the fermented medium is approximately 2 mg/L, which is not suitable for such purposes. It has also been reported that Gordonibacter pamelaeae DSM 19378 strain, which is a related species of Gordonibacter urolithinfaciens, has the capability to produce urolithin, but other enteric bacteria such as *Eggerthella lenta* DSM 2243 strain, *Eggerthella sinensis* DSM 16107 strain, and *Paraeggerthella honkongensis* DSM 16106 strain do not have the capability to produce urolithins (Non-Patent Document 7).

REFERENCES

Patent Literature

Patent Document 1: WO 2014/147280 pamphlet

Non-Patent Literature

Non-Patent Document 1: J. Agric. Food Chem. 56, 393-400 (2008)

Non-Patent Document 2: Mol. Nutr. Food Res. 58, 1199-1211 (2014)

Non-Patent Document 3: Biosci. Biotechnol. Biochem. 76, 395-399 (2012)

Non-Patent Document 4: J. Agric. Food Chem. 60, 8866-8876 (2012)

Non Patent Document 5: Mol. Nutr. Food Res. 55, S35-S43 (2011)

Non-Patent Document 6: Planta Med, 77, 1110-1115 (2011)

Non-Patent Document 7: Food Func., 5, 8, 1779-1784 (2014)

SUMMARY

The present invention aims to provide a novel microorganism that has a high capability to produce urolithins, and a method of producing urolithins using the same.

In order to solve the above problems, the present inventors diligently researched for the target microorganism and discovered a novel microorganism having a high capability to produce urolithins, and thereby arrived at the present invention.

The present invention is as follows.

[1] A microorganism that belongs to the genus *Eggerthella* and produces urolithins.

[2] The microorganism according to [1], wherein the microorganism produces urolithins using ellagic acid as a raw material.

[3] The microorganism according to [1] or [2], wherein the urolithins are urolithin C.

[4] The microorganism according to any one of [1] to [3], wherein the microorganism belonging to the genus *Eggerthella* is *Eggerthella* sp. DC 3563 (NITE BP-02376).

[5] A production method of urolithins, the method including the following step (a).

Step (a): producing urolithins from a raw material of the urolithins using a microorganism that belongs to the genus *Eggerthella* and has the capability to produce urolithins from the raw material of the urolithins, in a solution containing the raw material of the urolithins.

[6] The production method according to [5], wherein the raw material of the urolithins is ellagic acid.

[7] The production method according to [5] or [6], wherein the urolithins are urolithin C.

[8] The production method according to any one of [5] to [7], wherein step (a) is carried out in an environment in which a gas phase and/or a solution containing the raw material of the urolithins contains hydrogen.

[9] The production method according to any one of [5] to [8], wherein the solution containing the raw material of the urolithins further contains one or more types selected from the group of clathrate compounds consisting of α-cyclodextrin, β-cyclodextrin, γ-cyclodextrin, and derivatives thereof.

[10] The production method according to [9], wherein the clathrate compound is one or more types selected from the group consisting of β-cyclodextrin, γ-cyclodextrin, and derivatives thereof.

[11] A 16S rRNA gene of *Eggerthella* sp. DC 3563 (NITE BP-02376) represented by SEQ ID NO: 1.

According to the present invention, a novel microorganism having a high capability to produce urolithins, and an efficient method of producing urolithins using the same can be provided.

Furthermore, it is anticipated that antioxidant, anti-inflammatory, anti-glycation, and mitophagy-promoting effects and the like can be obtained using the urolithins obtained by the production method in, inter alia, cosmetic products, quasi drugs, medical products, sanitary products, pharmaceuticals, and food and beverage products (including supplements).

DETAILED DESCRIPTION

The present invention includes: an invention pertaining to a novel microorganism (first invention), an invention pertaining to a method for producing urolithins using the novel microorganism (second invention), and 16S rRNA gene of the novel microorganism (third invention).

1. First Invention

A first invention of the present invention is an invention pertaining to a novel microorganism. The novel microorganism is, specifically, a microorganism that belongs to the genus *Eggerthella* and produces urolithins. Hereinafter, the microorganism may be described as "the present microorganism" or the like.

Microorganism that Belongs to the Genus *Eggerthella* and Produces Urolithins

The first invention of the present invention is a microorganism that belongs to the genus *Eggerthella* and produces urolithins. The present microorganism is preferably the *Eggerthella* sp. DC 3563 (NITE BP-02376) strain. Hereinafter, the strain may be described as "the present strain", "DC 3563 strain", and the like.

The present strain is isolated from feces of a healthy human as an isolation source. The present strain was internationally deposited on 11 Nov. 2016 at NITE Patent Microorganisms Depositary (Office No. 122, 2-5-8 Kazusakamatari, Kisarazu-shi, Chiba-ken, Japan, 292-0818) of the National Institute of Technology and Evaluation (NITE) with the accession number of NITE BP-02376 under the Budapest Treaty.

Moreover, the present strain may also be a strain which is substantially equivalent thereto. A substantially equivalent strain refers to a strain that is a microorganism that belongs to the genus *Eggerthella* and produces urolithins, and that has the same level of high capability to produce urolithins as that of the present strain. The sequence of the 16S rRNA gene also exhibits homology with the sequence (SEQ ID NO: 1) of the 16S rRNA gene of the present strain of 98% or higher, preferably 99% or higher, and more preferably 100%, and preferably has the same bacteriological properties as that of the present strain. Furthermore, the present strain may be a strain that is grown from the present strain, or a strain substantially equivalent thereto, by a mutation treatment, genetic recombination, selection of a natural mutant strain, or the like.

The present microorganism has a high capability to produce urolithins in comparison to Gordonibacter urolithinfaciens, a known urolithin-producing bacteria. The capability to produce urolithins can be determined in the same manner as the method described in the examples.

The raw materials of the urolithins produced by the present microorganism are not particularly limited as long as urolithins are produced by the present microorganism using the raw materials, and examples thereof include ellagic acid; ellagitannins, such as punicalagin and geraniin, which are precursors of ellagic acid; and the like. Of these, ellagic acid is preferable because the production efficiency of urolithins by the present microorganism using ellagic acid is greater than the case where other raw materials are used. That is, the present microorganism produces urolithins using preferably ellagic acid as a raw material. The details described in the "Raw Materials of Urolithins" section of a second invention of the present invention described below apply to the raw materials of the urolithins.

Culture Conditions for a Microorganism that Belongs to the Genus *Eggerthella* and Produces Urolithins The present microorganism can be easily grown, for example, by culturing. The method thereof is not particularly limited as long as the present microorganism can be grown, and a method commonly used to grow the present microorganism can be appropriately changed as necessary and used. Examples thereof are described below, but the present microorganism can also be cultured by each of the aspects described in the "Production of Urolithins" section of the second invention of the present invention described below.

The culture temperature for the present microorganism is preferably not lower than 20° C., more preferably not lower than 25° C., and even more preferably not lower than 30° C., and is preferably not higher than 42° C., more preferably not higher than 40° C., and even more preferably not higher than 37° C. The culture medium is not particularly limited, and a commonly used culture medium can be appropriately changed as necessary and used. For example, an ANAEROBE BASAL BROTH (ABB) culture medium available from OXIO, a Wilkins-Chalgren Anaerobe Broth (CM0643) available from Oxoid Limited, and a GAM culture medium and a modified GAM culture medium available from Nissui Pharmaceutical Co., Ltd. can be used.

Furthermore, a water soluble organic material can be added as a carbon source, for example. Examples of the water soluble organic material include the following compounds: saccharides such as sorbose, fructose, glucose, and dextrose; alcohols such as methanol; and organic acids such as valeric acid, butyric acid, propionic acid, acetic acid, and formic acid.

The concentration of organic material added in the culture medium as a carbon source can be adjusted, as appropriate, for efficient growth. Typically, the concentration can be selected in a range from 0.1 to 10 wt/vol %.

In addition to the carbon source described above, a nitrogen source is added to the culture medium. Various nitrogen compounds that may be used ordinarily in cultivation or fermentation can be used as the nitrogen source.

Preferred inorganic nitrogen sources are ammonium salts and nitrates. More preferable examples include ammonium sulfate, ammonium chloride, ammonium phosphate, ammonium hydrogen phosphate, triammonium citrate, potassium nitrate and sodium nitrate.

On the other hand, examples of preferred organic nitrogen sources include amino acids, yeast extracts, peptones (for example, polypeptone N), meat extracts (for example, Lab Lemco powder, bouillon, etc.), liver extracts, and digested serum. Examples of more preferable organic nitrogen sources include arginine, cysteine, citrulline, lysine, yeast extract, and peptones (for example, polypeptone N).

Furthermore, other organic materials or inorganic materials can also be added to the culture medium in addition to the carbon source and the nitrogen source. For example, in some cases, growth and activity can be enhanced by adding cofactors such as vitamins or inorganic compounds such as various salts to the culture medium. Examples of plant- and animal-derived cofactors for microbial growth, such as inorganic compounds and vitamins, include the following.

| Inorganic Compounds | Vitamins |
|---|---|
| Potassium dihydrogen phosphate | Biotin |
| Magnesium sulfate | Folic acid |
| Manganese sulfate | Pyridoxine |
| Sodium chloride | Thiamine |
| Cobalt chloride | Riboflavin |
| Calcium chloride | Nicotinic acid |
| Zinc sulfate | Pantothenic acid |
| Copper sulfate | Vitamin B12 |
| Potassium alum | Thioctic acid |
| Sodium molybdate | p-aminobenzoic acid |
| Potassium chloride | |
| Boric acid, etc. | |
| Nickel chloride | |
| Sodium tungstate | |
| Sodium selenate | |
| Iron (II) ammonium sulfate | |
| Sodium acetate trihydrate | |
| Magnesium sulfate heptahydrate | |
| Manganese sulfate tetrahydrate | |

Methods for producing a culture solution by adding plant- and animal-derived growth cofactors such as these inorganic compounds and vitamins are well known. The culture medium can be a liquid, a semi-solid, or a solid. A preferred form of the culture medium is a liquid culture medium.

Resting Bacterial Cells of Microorganisms Belonging to the Genus *Eggerthella*

The present microorganism includes resting bacterial cells thereof. A resting bacterial cell refers to a bacterial cell obtained by removing culture medium components from a cultured microorganism by manipulations such as centrifugation, and washing the microorganism with water, a salt solution such as saline, or a buffer solution such that the bacterial cells are suspended in the washing solution or the like. In the first invention of the present invention, a resting bacterial cell is a bacterial cell having a metabolic system that produces urolithins. The buffer solution is preferably a phosphate buffer solution, a tris-hydrochloric acid buffer solution, a citrate-phosphate buffer solution, a citrate buffer solution, a MOPS buffer solution, an acetate buffer solution, a glycine buffer solution, and the like. A buffer solution for which the pH and concentration have been appropriately adjusted in accordance with known methods can be used.

Urolithins

Urolithins are known substances having a structure represented by General Formula (1). For example, as shown in Table 1, urolithins are known to include urolithin A, urolithin B, urolithin C, urolithin D, urolithin E, urolithin M3, urolithin M4, urolithin M5, urolithin M6, urolithin M7, and isourolithin A, depending on different R1 to R6 in the chemical formula.

In the first invention of the present invention, the urolithin is preferably urolithin C because of the high production efficiency thereof by the present microorganism.

Chemical Formula 1

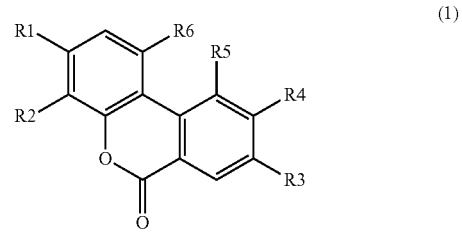

(1)

TABLE 1

| | \multicolumn{6}{c|}{Types of Urolithin} |
|---|---|---|---|---|---|---|
| | R1 | R2 | R3 | R4 | R5 | R6 |
| Urolithin A | —OH | —H | —OH | —H | —H | —H |
| Urolithin B | —OH | —H | —H | —H | —H | —H |
| Urolithin C | —OH | —H | —OH | —OH | —H | —H |
| Urolithin D | —OH | —OH | —OH | —OH | —H | —H |
| Urolithin E | —OH | —OH | —OH | —H | —OH | —H |
| Urolithin M3 | —OH | —H | —OH | —OMe | —H | —H |
| Urolithin M4 | —OH | —H | —OMe | —OH | —H | —H |
| Urolithin M5 | —OH | —OH | —OH | —OH | —OH | —H |
| Urolithin M6 | —OH | —H | —OH | —OH | —OH | —H |
| Urolithin M7 | —OH | —H | —OH | —H | —OH | —H |
| Isourolithin A | —OH | —H | —H | —OH | —H | —H |

2. Second Invention

A second invention of the present invention is a method of producing urolithins using a microorganism that belongs to the genus *Eggerthella* and has the capability to produce urolithins.

The second invention of the present invention includes the following step (a), but may also include other steps.

(1) Step (a)

Step (a): producing urolithins from a raw material of the urolithins using a microorganism that belongs to the genus *Eggerthella* and has the capability to produce urolithins from the raw material of the urolithins, in a solution containing the raw material of the urolithins.

Microorganism Belonging to the Genus *Eggerthella*

The description of the first invention of the present invention applies to the microorganism belonging to the genus *Eggerthella* of the second invention of the present invention.

Solution Containing a Raw Material of the Urolithins

The solution containing the raw materials of the urolithins according to the second invention of the present invention is not particularly limited as long as the solution enables the present microorganism having the capability to produce urolithins from the raw materials of the urolithins to produce urolithins from the raw material of the urolithins in the solution thereof. The solution is preferably a culture medium, and can be an aspect described in the "Culture Conditions for a Microorganism that Belongs to the Genus *Eggerthella* and Produces Urolithins" section above.

Note that in each case, "culture medium" as described herein refers to a solution in which the present microorganism can grow, including minimal media, and does not include a solution in which the present microorganism cannot grow, such as, for example, a salt solution or a buffer solution described above.

A salt solution or a buffer solution described above is preferable as a solution containing the raw materials of the urolithins for cases in which the present microorganisms are resting bacterial cells.

Raw Materials of Urolithins

The raw materials of the urolithins are not particularly limited as long as urolithins are produced by the present microorganism using the raw materials, and examples thereof include ellagic acid; ellagitannins, such as punicalagin and geraniin, which are precursors of ellagic acid. Of these, ellagic acid is preferable because the production efficiency of urolithins by the present microorganism using ellagic acid is greater than the case where other raw materials are used. Here, ellagitannins such as punicalagin and geraniin may be extracted from plants and hydrolyzed to ellagic acid, or the ellagic acid itself may be extracted.

The raw materials of the urolithins may be added prior to production of the urolithins to a solution or a solvent that is to be a solution containing the raw materials of the urolithins, or may be added to the solution during the production of the urolithins. Here, the raw materials may be added all at once, sequentially, or continuously.

The content of the raw material in the solution containing the raw materials of the urolithins is ordinarily not less than 0.01 g/L, preferably not less than 0.1 g/L, and more preferably not less than 1.0 g/L. On the other hand, the content thereof is ordinarily not greater than 100 g/L, preferably not greater than 20 g/L, and more preferably not greater than 10 g/L.

The plants that produce ellagic acid and/or ellagitannins are not particularly limited, and examples thereof include pomegranates, raspberries, blackberries, cloudberries, boysenberries, strawberries, walnuts, and Geranium thunbergii. Of these, due to a high content of ellagic acid and/or ellagitannins, pomegranates, boysenberries, and eranium thunbergii are preferable, and pomegranates are more preferable.

Any one type of these plants may be used alone, or two or more types may be used in combination. Furthermore, the method and conditions for the extraction of ellagic acid and/or ellagitannins from plants are not particularly limited, and the extraction may be performed by a known method. For example, known extraction methods such as water extraction, hot water extraction, warm water extraction, alcohol extraction, and supercritical extraction can be used.

When solvent extraction is performed, examples of solvents include water; alcohols (anhydrous or hydrous) such as lower alcohols such as methanol and ethanol, and polyhydric alcohols such as propylene glycol and 1,3-butylene glycol; ketones such as acetone, esters such as diethyl ether, dioxane, acetonitrile, and ethyl acetate; and xylene, and the solvent is preferably water, ethanol, or the like. Any one type of these solvents may be used alone, or two or more types may be used in combination.

The method of hydrolysis of extracted ellagitannins such as punicalagin to ellagic acid is not particularly limited, but examples include methods of hydrolysis using acids, enzymes, and microorganisms.

The obtained ellagic acid and/or ellagitannins can be used directly, but may also be subjected to desiccation to form a powder. Also, as necessary, the obtained ellagic acid and/or ellagitannins may be subjected to, inter alia, purification and concentration treatments. As the purification treatment, treatments of filtration, adsorption using, inter alia, ion exchange resins or activated carbon columns, and bleaching can be performed. In addition, a known method such as the one using an evaporator can be used as the concentration treatment. The obtained ellagic acid and/or ellagitannins (or a purified product or concentrate thereof) may be subjected to pulverization in accordance with known methods such as a pulverization method for lyophilization process, or a pulverization method by spray drying with addition of excipients such as dextrin, corn starch, and gum arabic. Subsequently, the powder may be dissolved, as necessary, in pure water, ethanol, or the like for use.

Any commercially available food or beverage product or the like can be used as long as the product contains ellagic acid and/or an ellagitannin. For example, pomegranate extract, concentrated pomegranate fruit juice, and pomegranate juice can be used.

Urolithins

The above description of the urolithins according to the first invention of the present invention is incorporated with regard to the urolithins of the second invention of the present invention.

Production of Urolithins Using the Present Microorganism

The present microorganism produces urolithins through cultivation in a solution containing the raw materials of the urolithins by a method suitable for the production of urolithins.

The solution is preferably a culture medium (culture solution), and the description described in the first invention of the present invention is applied as an aspect thereof. Note that a case in which the resting bacterial cells of the present microorganism are used will be described later.

Furthermore, the method suitable for producing urolithins can be used by appropriately modifying, as necessary, a method that is commonly used for growing the present microorganisms.

In industrial production, a continuous cultivation system (continuous fermentation system) that is capable of continuously feeding the culture medium and gaseous substrate and is provided with a mechanism for recovering the culture can be used.

As an incubator, a commonly used culture vessel can be used directly. Culture vessels that can be used in the cultivation of the present microorganisms are commercially available. An anaerobic atmosphere can be created by replacing oxygen that mixes into the culture vessel with an inert gas such as nitrogen or a substrate gas.

In cultivation of the present microorganisms, additional functions can be imparted to the culture vessel. For example, in addition to an ordinarily used stirring and mixing vessel, a bubble column type or a draft tube type culture vessel can also be used. The present microorganisms are freely dispersed by circulation of a mixed gas into the liquid culture medium, and contact between the microorganisms and the culture medium can be sufficiently obtained. Alternatively, as with a biotrickling filter, the microorganisms are allowed to grow while dripping water into a carrier layer of a slag having high permeability, other inorganic ceramic filler, or synthetic organic substances such as polypropylene, and the microorganisms can be cultured while circulating a gas. Furthermore, the present microorganisms that are used can be immobilized in a carrageenan gel, alginate gel, acrylamide gel, chitin, cellulose, agar, and the like by an ordinary method for use.

Depending on the shape of the culture vessel, a stirrer or the like can be used to sufficiently stir the culture medium. The production efficiency of urolithins can be optimized by stirring the culture in the culture vessel to thereby increase the opportunities for contact of the components of the culture medium and the gaseous substrate with anaerobic microorganisms. The gaseous substrate can also be supplied as nanobubbles.

For sufficient growth of the microorganisms, the pH of the culture is preferably 6.0 or greater, more preferably 6.5 or greater, and even more preferably 6.8 or greater, and preferably not greater than 8.5, more preferably not greater than 8.0, and even more preferably not greater than 7.5.

In addition, the temperature of the culture vessel is not particularly limited, but in order to increase the yield of urolithins, the temperature thereof is preferably not lower than 20° C., more preferably not lower than 25° C., and even more preferably not lower than 30° C., but preferably not higher than 42° C., more preferably not higher than 40° C., and even more preferably not higher than 37° C.

The cultivation period can be set as appropriate in accordance with, inter alia, the production amount of the urolithins and the residual amount of raw material. The cultivation period is usually not less than 8 hours, preferably not less than 12 hours, and more preferably not less than 16 hours, but usually not greater than 340 hours, preferably not greater than 240 hours, and more preferably not greater than 170 hours. However, the cultivation period is not limited thereto.

The culture medium can also be supplied continuously to efficiently yield the urolithins. The amount of fresh culture medium supplied to the culture vessel is such that the dilution rate of the culture in the culture vessel is preferably 0.04/hr or greater, and more preferably 0.08/hr or greater, but preferably not greater than 2/hr, and more preferably not greater than 1/hr.

The gas phase and aqueous phase (solution containing a raw material of urolithins) of the culture solution preferably do not contain air or oxygen, and examples include gas and aqueous phases that contain nitrogen and/or hydrogen in any ratio, and gas and aqueous phases that contain nitrogen and/or carbon dioxide in any ratio, and the gas phase and aqueous phase preferably contain hydrogen.

The proportion of hydrogen in the gas phase is usually not less than 0.1%, preferably not less than 1%, and more preferably not less than 2%, but usually not greater than 100%, preferably not greater than 50%, and more preferably not greater than 20% due to the promotion of production of urolithins at such ratios.

The method of establishing such an environment for the gas phase and aqueous phase is not particularly limited, and methods such as, for example, replacing the gas phase with the above-mentioned gas prior to cultivation, supplying from the bottom of the incubator during cultivation, supplying to the gas phase part of the incubator, and bubbling the aqueous phase with the above-mentioned gas prior to cultivation can be adopted. The supplied amount of gas is usually not less than 0.005 vvm, preferably not less than 0.05 vvm, but usually not greater than 2 vvm, and preferably not greater than 0.5 vvm. The mixed gas can also be supplied as nanobubbles. Note that "vvm" in the present specification refers to the ratio of supplied amount of gas relative to volume of liquid per minute, and for example, 2 vvm of gas supplied relative to 10 L of the aqueous phase means a gas supply of 20 L/min.

Furthermore, as the hydrogen, hydrogen gas may be used directly, but a hydrogen precursor such as formic acid or its salts may be added to the aqueous phase.

The pressurization condition for cultivation of the present microorganisms is not particularly limited as long as the condition allows for growth. A preferred pressurization condition may include, but is not limited to, under a pressure in a range from 0.02 to 0.2 MPa.

In addition, in some cases, the production of urolithins can be promoted by adding, inter alia, a surfactant, an adsorbent, or a clathrate compound to the aqueous phase.

Examples of the surfactant include Tween 80, and can be added at an amount of approximately from 0.001 g/L to 10 g/L.

Examples of the adsorbent include cellulose and derivatives thereof; dextrin; hydrophobic adsorbents Diaion HP series and Sepabeades series, available from Mitsubishi Chemical Corporation; and Amberlite XAD series, available from Organo Corporation.

Examples of the clathrate compound may include α-cyclodextrin, β-cyclodextrin, γ-cyclodextrin, cluster dextrins (highly branched cyclic dextrins), and derivatives thereof. Also, in some cases, the production of urolithins can be further promoted through co-presence of two or more clathrate compounds.

In terms of a total molar ratio of the clathrate compounds to the raw material of urolithins, the amount of the clathrate compound added is usually 0.2 equivalents or greater, preferably 1.0 equivalents or greater, and more preferably 2.0 equivalents or greater, and usually 10.0 equivalents or less, preferably 5.0 equivalents or less, and more preferably 4.0 equivalents or less.

Production of Urolithins Using Resting Bacterial Cells of the Present Microorganisms In the case where the present microorganisms are resting bacterial cells, the salt solution or buffer described in the aforementioned "Resting Bacterial Cells of Microorganisms Belonging to the Genus *Eggerthella*" section is preferred as the solution containing the raw materials of urolithins in place of the culture medium. For other conditions, the description of the above "Production of Urolithins Using the Present Microorganism" section is incorporated.

Other Steps

In addition to the above steps, the second invention of the present invention may include a yield measurement step of urolithins, a purification step of the produced urolithins, and other necessary steps.

Yield Measurement Step of Urolithins

The yield of urolithins varies depending on the production conditions, but is usually 0.005 g or greater, preferably 0.1 g or greater, and more preferably 1 g or greater, per 1.0 L of the solution after the production of urolithins. On the other hand, the upper limit is not particularly limited, but is usually not greater than 20 g, preferably not greater than 15 g, and more preferably not greater than 10 g.

The production of urolithins can be confirmed by quantitatively determining the amounts of raw materials and urolithins in the solution after production of the urolithins. An example of this is presented below.

For example, ethyl acetate, to which an acid such as formic acid has been added as necessary, is added to the solution after the production of urolithins, the mixture is vigorously stirred and then centrifuged, and the ethyl acetate layer is extracted. The same operation can be performed several times on the solution as necessary, and the extracted ethyl acetate layers can be combined to obtain a liquid extract of urolithins. The liquid extract is concentrated under reduced pressure using an evaporator or the like, dried, and dissolved in methanol. The obtained solution is filtered using a membrane such as a polytetrafluoroethylene (PTFE) membrane to remove insoluble matter, and the resulting product can be used as a sample for high performance liquid chromatography (HPLC). Conditions for high performance liquid chromatography include, but are not limited to, the following.

Conditions for High Performance Liquid Chromatography
   Column: Inertsil ODS-3 (250×4.6 mm) (available from GL Science)
   Eluent: water/acetonitrile/acetic acid=74/25/1
   Flow rate: 1.0 mL/min
   Column temperature: 40° C.
   Detection: 305 nm
Purification Step of the Produced Urolithins The produced urolithins can be used as is, but may also be subjected to desiccation to form a powder. Also, as necessary, the obtained urolithins may be subjected to, inter alia, purification and concentrating treatments. As the purification treatment, treatments of filtration, adsorption using, inter alia, ion exchange resins or activated carbon columns, and bleaching can be performed. In addition, a known method such as the one using an evaporator can be used as the concentration treatment. Furthermore, the obtained urolithins (or a purified product or concentrate thereof) may be subjected to pulverization in accordance with known methods such as a pulverization method for lyophilization process, or a pulverization method by spray drying with addition of excipients such as dextrin, corn starch, and gum arabic. Subsequently, the powder may be dissolved, as necessary, in pure water, ethanol, or the like for use.

The urolithins obtained by such methods after a heating and desiccation treatment, a spray drying treatment, or a lyophilization treatment are usually present at an amount of from 1 to 50 mass % as a total amount of urolithins in the dry powder. Additionally, for example, the content is preferably expressed in mass % of a concentration range in which a pair of concentrations in mass % selected from 1%, 2%, 3%, 4%, 5%, 6%, 7%, 8%, 9%, 10%, 20%, 30%, 40%, and 50% are used as the lower limit (X or greater, or, greater than X) and the upper limit (Y or less, or, less than Y), respectively.

3. Third Invention

A third invention of the present invention is the 16S rRNA gene of *Eggerthella* sp. DC 3563 (NITE BP-02376) represented by SEQ ID NO: 1. Methods for determining the sequence of the 16S rRNA gene are known. The sequence was identified by the method described in the examples.

EXAMPLES

The present invention is described in further detail below through specific examples; however, the examples are by no means intended to limit the present invention.

Example 1

Strain Isolation, Taxonomic Properties

Isolation and the taxonomic properties of the strain of *Eggerthella* sp. DC 3563 (NITE BP-02376) are described below.

To isolate the present strain, ellagic acid was added in a final concentration of 1 g/L to an ABB culture medium (available from Oxoid Limited), after which the mixture was heat sterilized, the gas phase was purged with a gas of $N_2:CO_2:H_2$ (80%/10%/10%), and the resulting product was used as a basal medium. The basal medium was inoculated with human feces and cultured at 37° C. under anaerobic conditions. The culture solution after cultivation was diluted and spread onto an ABB agar culture medium. A single colony were obtained by cultivation at 37° C. under anaerobic conditions. Each bacteria was inoculated into the basal medium and cultured at 37° C. under anaerobic conditions.

The amount of urolithins in the culture broth after cultivation was quantitatively determined by the following method.

Urolithins were extracted from 5 mL of the culture broth with an equal amount of ethyl acetate, and the resulting ethyl acetate phase was concentrated under reduced pressure and dried to obtain a solid. The dry solid obtained in this manner was re-dissolved in 0.5 mL of methanol, and the amount of urolithins was quantitatively analyzed through HPLC.

HPLC was performed under the conditions described below.

HPLC Analysis Conditions:
   Column: Inertsil ODS-3 (250×4.6 mm) (available from GL Science)
   Eluent: water/acetonitrile/acetic acid=74/25/1
   Flow rate: 1.0 mL/min
   Column temperature: 40° C.
   Detection: 305 nm As a reference sample, urolithins available from DALTON PHARMA were dissolved in DMSO before use. The present strain of *Eggerthella* sp. DC 3563 (NITE BP-02376) was obtained as a microorganism that converts the added ellagic acid to urolithin C through cultivation for two weeks.

The bacteriological properties of DC 3563 strain analyzed using known methods are summarized in Table 2.

TABLE 2

| Cultivation temperature | | Grow at 30 to 45° C. |
|---|---|---|
| Cell morphology | | Bacilli |
| Gram stainability | | + |
| Presence of spores | | − |
| Motility | | − |
| Catalase | | + |
| Oxidase | | − |
| Urease | | − |
| Hydrolyzability of gelatin | | − |
| Hydrolysis of esculin | | − |
| Indole production | | − |
| Oxidation test of carbon source | Glucose | − |
| | D-mannitol | − |
| | Lactose | − |
| | Saccharose | − |
| | Maltose | − |
| | Salicin | − |
| | D-xylose | − |
| | L-arabinose | − |
| | Glycerin | − |
| | D-cellobiose | − |
| | D-mannose | − |
| | D-melezitose | − |
| | D-raffinose | − |
| | D-sorbitol | − |
| | L-rhamnose | − |
| | D-trehalose | − |

The present disclosure relates generally to the field of agriculture. In particular, the present disclosure relates to compositions and methods for controlling pathogens that have a deleterious effect in agriculture, including in crop cultivation or in livestock production.

Example 2

Strain Identification

DNA was extracted from DC 3563 strain, which was the present strain, full-length 16S rRNA gene was amplified by PCR using a universal primer for 16S rRNA genes, and the 16S rRNA gene sequence of the present strain was determined (SEQ ID NO: 1).

A homology search was performed using the DNA Data Bank of Japan (DDBJ), and DC 3563 strain, which was the present strain, exhibited 99.9% homology with *Eggerthella lenta* JCM 9979 (AB558167) strain.

In addition, sequences obtained from the Nucleic Acid Database for each standard strain of bacterial strains that are highly homologous to the present strain were subjected to multiple alignment, after which a molecular phylogenetic tree was prepared through the NJ method, and as a result, DC 3563 strain, which is the present strain, formed a cluster with the bacterial strain constituted of the genus *Eggerthella* and was shown to be a related species.

It was determined, as the comprehensive results of analysis of the above forms, assimilability, and 16S rRNA gene, that DC 3563 strain, which is the present strain, was identified to be a microorganism belonging to the genus *Eggerthella* sp.

Example 3

Production of Urolithins (Fermentation)

The basal medium described in Example 1 was inoculated with DC 3563 strain, which is the present strain, and cultured at 37° C. under anaerobic conditions for 2 weeks. After the cultivation was completed, the urolithins were quantitatively analyzed by the method described in Example 1.

The result shows that urolithin C was obtained in a molar yield of 90.3% with respect to the added ellagic acid.

Example 4

Example 4 was prepared in the same manner as Example 1 with the exception that a product obtained by further adding 2.4 equivalents of β-cyclodextrin in a molar ratio with respect to the ellagic acid to the basal medium described in Example 1, a product obtained by further adding 2.4 equivalents of γ-cyclodextrin in a molar ratio from the ellagic acid to the basal medium described in Example 1, or a product in which these were not added was used.

The result shows that in a case where cyclodextrin was not added to the added ellagic acid, urolithin C was obtained in a molar yield of 26.6%. In a case where β-cyclodextrin was added, urolithin C was obtained in a molar yield of 30.2%. In a case where γ-cyclodextrin was added, urolithin C was obtained in a molar yield of 31.9%.

The novel microorganism of the present invention has a higher capability to produce urolithins than known microorganisms capable of producing urolithins. With the method for producing urolithins using the microorganism, urolithins can be produced more efficiently than with known methods for producing urolithins using microorganisms.

Cosmetic products, quasi drugs, medical products, sanitary products, pharmaceuticals, food and beverage products (including supplements) and the like that use urolithins are used to exert antioxidant, anti-inflammatory, and anti-glycation effects and the like.

All the prior art documents cited in the present specification are hereby incorporated as references.

What is claimed is:

1. A production method of urolithins, the method comprising the following steps (a) and (b),
   step (a): culturing in vitro in a culture medium a microorganism with a raw material, wherein the microorganism comprises a 16S rRNA gene that exhibits sequence homology of 99% or higher with a sequence of the 16S rRNA gene of *Eggerthella* sp. DC 3563 (NITE BP-02376) having a sequence as set forth in SEQ ID NO: 1, and wherein the microorganism has a capability to produce urolithins from the raw material; and
   step (b): purifying the produced urolithins.

2. The production method according to claim 1, wherein the raw material is ellagic acid.

3. The production method according to claim 1, wherein the urolithins are urolithin C.

4. The production method according to claim 1, wherein step (a) is carried out in an environment in which a gas phase and/or a solution containing the raw material of the urolithins contains hydrogen.

5. The production method according to claim 1, wherein the culture medium further contains one or more types of clathrate compounds selected from the group consisting of α-cyclodextrin, β-cyclodextrin, γ-cyclodextrin, and derivatives thereof.

6. The production method according to claim 5, wherein the clathrate compound is one or more types selected from the group consisting of β-cyclodextrin, γ-cyclodextrin, and derivatives thereof.

7. The production method according to claim 1, wherein the raw material is present in the culture medium in an amount ranging from about 1 g/L to about 10 g/L.

8. The production method according to claim 1, wherein the culturing is performed at a pH ranging from about 6.8 to about 7.5.

9. The production method according to claim 1, wherein the culturing is performed at a temperature ranging from about 25° C. to about 37° C.

10. The production method according to claim 1, wherein the culturing is performed for a duration ranging from about 16 hours to about 170 hours.

11. The production method according to claim 1, wherein the urolithins are produced in an amount of about 1 gram or greater per liter of culture medium.

12. The production method according to claim 1, wherein the culture medium is anaerobe basal broth (ABB).

13. The production method according to claim 1, wherein the purifying comprises extraction with ethyl acetate.

* * * * *

UNITED STATES PATENT AND TRADEMARK OFFICE
CERTIFICATE OF CORRECTION

PATENT NO. : 11,168,300 B2
APPLICATION NO. : 16/536056
DATED : November 9, 2021
INVENTOR(S) : Masatake Kudoh Page 1 of 1

It is certified that error appears in the above-identified patent and that said Letters Patent is hereby corrected as shown below:

In the Specification

Column 2, Lines 4-5, delete "honkongensis" and insert -- hongkongensis --.

Column 7, Line 35, delete "eranium" and insert -- Geranium --.

Column 10, Line 9, delete "Sepabeades" and insert -- Sepabeads --.

Signed and Sealed this
First Day of March, 2022

Drew Hirshfeld
*Performing the Functions and Duties of the
Under Secretary of Commerce for Intellectual Property and
Director of the United States Patent and Trademark Office*